United States Patent [19]
Montgomery et al.

[11] Patent Number: 5,840,958
[45] Date of Patent: Nov. 24, 1998

[54] 1S TO 1R EPIMERIZATIONS OF PYRETHROID INTERMEDIATES

[75] Inventors: Ronald E. Montgomery, Yardley; Leland A. Smeltz, Langhorne, both of Pa.

[73] Assignee: FMC Corporation, Philadelphia, Pa.

[21] Appl. No.: 950,819

[22] Filed: Oct. 15, 1997

Related U.S. Application Data

[60] Provisional application No. 60/028,698 Oct. 17, 1996.

[51] Int. Cl.$^6$ .................................................. C07C 51/353
[52] U.S. Cl. .......................... 560/124; 562/506; 562/866; 562/867
[58] Field of Search ............................. 560/124; 562/506, 562/866, 807

[56] References Cited

U.S. PATENT DOCUMENTS

| | | | |
|---|---|---|---|
| 4,008,268 | 2/1977 | Mizutani et al. | 260/514 H |
| 4,024,163 | 5/1977 | Elliott et al. | 260/347.4 |
| 4,261,921 | 4/1981 | Smeltz | 260/465 D |
| 4,874,473 | 10/1989 | Arlt et al. | 560/124 |
| 4,954,651 | 9/1990 | Suzukamo et al. | 562/856 |
| 4,962,233 | 10/1990 | Hagiya et al. | 560/124 |
| 4,977,970 | 12/1990 | Steiger | 180/6.2 |
| 5,164,411 | 11/1992 | Baum et al. | 514/521 |

OTHER PUBLICATIONS

Elliott, M. et al., "Potent Pyrethroid Insecticides from Modified Cyclopropane Acids", *Nature*, 1973, 244, 456–457.

*Primary Examiner*—James H. Reamer
*Attorney, Agent, or Firm*—Woodcock Washburn Kurtz Mackiewicz & Norris LLP

[57] ABSTRACT

This invention relates to a process for preparing certain isomers of 2,2-dimethyl-3-(2,2-disubstitutedvinyl) cyclopropanecarboxylic acid or derivatives thereof. More specifically it relates to the epimerization of the 1S cyclopropanecarboxylic acid and its derivatives into the corresponding 1R isomers.

10 Claims, No Drawings

1S TO 1R EPIMERIZATIONS OF PYRETHROID INTERMEDIATES

This application claims the benefit of U.S. Provisional application Na 60/028,698, filed Oct. 17, 1996.

This invention relates to a process for preparing certain isomers of 2,2-dimethyl-3-(2,2-disubstitutedvinyl) cyclopropanecarboxylic acid or derivatives thereof. More specifically it relates to epimerizations of the 1S cyclopropanecarboxylic acid and its derivatives into the corresponding 1R isomers. Most specifically it relates to the epimerization of 1S-trans into 1R-cis and the epimerization of 1S-cis into 1R-trans cyclopropanecarboxylic acids and derivatives. The products of the epimerizations are useful for preparing pyrethroids that have enhanced insecticidal activity.

Pyrethroid esters of 2,2-dimethyl-3-(2,2-dichlorovinyl) cyclopropanecarboxylic acid (DV acid) are important commercial insecticides. These pyrethroids are typically prepared as mixtures of isomers due to the chiral centers at positions 1 and 3 of the cyclopropane ring. The two chiral centers can lead to four possible isomers: 1S-trans, 1R-cis, 1S-cis, and 1R-trans. Cis and trans refer to the relative stereochemistry of the carboxyl and vinyl groups at cyclopropane positions 1 and 3 respectively, and 1R and 1S refer to the absolute stereochemistry at position 1. A change in absolute stereochemistry at a given position, for example from 1S to 1R in the structures below, is known as an epimerization.

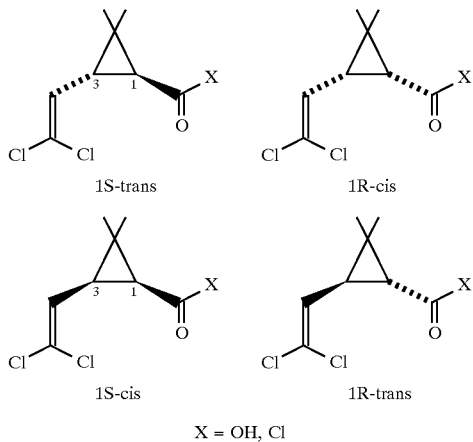

X = OH, Cl

Esterification of a cis:trans racemic mixture of DV acid chloride with either 3-phenoxybenzyl alcohol or the cyanohydrin of 3-phenoxybenzaldehyde leads to the commercially useful pyrethroids permethrin or cypermethrin, respectively. As discussed below, the different isomers in each of these pyrethroid products differ with respect to their activities in both insect and mammalian systems, and it would be useful to convert one isomer into another that is either more insecticidal and/or safer to non-target species.

Trans isomers of permethrin and cypermethrin are reported to have lower mammalian toxicity than the corresponding cis isomers (Nature 244, 456, 1973). Preparations of trans DV acid or the acid halide or lower alkyl anhydride thereof by isomerization of the corresponding cis DV acid derivatives are known. U.S. Pat. No. 4,008,268, incorporated herein by reference, describes the conversion of a 45:55 cis/trans mixture of DV acid to about 20:80 by heating the mixture to 160°–165° C. in the presence of an acid catalyst such as p-toluenesulfonic acid and either acetic anhydride or thionyl chloride. A higher percentage of the trans isomers can be obtained by isomerizing the cis DV acid halide in the presence of an aryl phosphine, as described in U.S. Pat. No. 4,954,651, also incorporated herein by reference. While the above methods are reported to be useful for obtaining trans isomers, they are not directed at obtaining a specific configuration at the 1 position of the cyclopropane ring.

With regard to the insecticidal activity of the isomeric constituents of permethrin or cypermethrin, the isomer having the 1R configuration for either the cis or trans pyrethroid is more insecticidally active than the corresponding isomer having the 1S configuration, with the 1R-cis isomer being the most potent (U.S. Pat. No. 5,164,411 and 4,997,970). The insecticidal potency of the 1S pyrethroid isomer is many-fold less active than the corresponding 1R isomer. The most insecticidal isomer of cypermethrin is the S-α-cyano-m-phenoxybenzyl ester of 1R-cis DV (the ÖSÖ in ÖS-α-cyanoÖ refers to the absolute stereochemistry at the carbon to which the cyano group is attached).

The isomer having the 1R configuration is also more insecticidally potent than the 1S isomer of pyrethroid esters wherein the dichlorovinyl group is replaced by a dibromovinyl group (U.S. Pat. No. 4,024,163). Of the eight possible isomers of α-cyano-m-phenoxybenzyl-3-(2,2-dibromovinyl)-2,2-dimethylcyclopropanecarboxylate, the most insecticidal is (S)-α-cyano-m-phenoxybenzyl (1R-cis) -3-(2,2-dibromovinyl)-2,2-dimethylcyclopropane carboxylate (deltamethrin). Thus, the optimum stereochemistry for insecticidal activity of 3-phenoxybenzyl or α-cyano-3-phenoxybenzyl esters of dihalovinylcyclopropylcarboxylic acids is the same when the vinyl halogens are either bromine or chlorine.

SUMMARY OF THE INVENTION

This invention relates to a process for the epimerization of compounds represented by formula I:

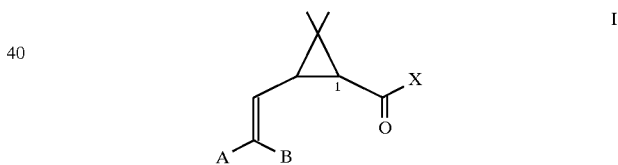

where both A and B are chlorine or bromine, or one of A and B is chlorine and the other is trifluoromethyl; and X is selected from halogen, OH, and $O_2$C-alkyl. In the process, epimerization of certain 1S-trans dimethyl-3-(2,2-disubstitutedvinyl)-cyclopropanecarboxylic acids and derivatives thereof enhances the content of the corresponding 1R-cis isomer and epimerization of certain 1S-cis dimethyl-3-(2,2-disubstitutedvinyl)-cyclopropanecarboxylic acids and derivatives thereof enhances the content of the corresponding 1R-trans isomer.

DESCRIPTION OF THE INVENTION

The methods of the present invention, describing the epimerization of 1S-trans to 1R-cis and 1S-cis to 1R-trans, are directed at both the relative and absolute stereochemistry of the cyclopropane ring. The conversions described herein are stereospecific in that position 3 of the cyclopropane ring is unaffected. The 1S dimethyl-3-(2,2-disubstitutedvinyl) cyclopropanecarboxylic acids and derivatives capable of undergoing epimerization to the corresponding 1R compounds in accordance with the present process are represented by formula I above.

In the present process, the 1S-trans or 1S-cis-dimethyl-3-(2,2-disubstitutedvinyl) cyclopropanecarboxylic acid or anhydride is heated at a temperature between 140°–170° C. in the presence of a suitable catalyst. Suitable catalysts are protic acids such as toluenesulfonic acid, sulfuric acid or the like. The amount of catalyst used is about 1% to 10% by weight based on the weight of acid or anhydride of formula I (X is OH or $O_2C$-alkyl). The alkyl portion of the $O_2C$-alkyl group may be from one to six carbons. A preferred anhydride for isomerization is I where X is $O_2CCH_3$. This anhydride may be formed in situ starting with the DV acid and acetylchloride. Reaction times are typically at least about one hour to up to several hours.

If the corresponding acid halide (I, X is Cl or Br) is employed as the starting material, the epimerization process may be performed with or without solvent. The acid halide is heated at a temperature between about 140°–170° C., preferably between about 145°–150° C. Reaction times are typically at least about one-half hour to up to several hours, and preferably about three to four hours. The use of a Lewis acid catalyst in the mixture to be epimerized, such as the Lewis acids described in U.S. Pat. No. 4,954,651, is optional. In the present process, it is preferred to carry out the epimerization process by heating the acid halide without solvent and without added catalyst.

When the 1S-trans DV acid chloride is heated at 145°–150° C. for four hours, the resulting isomeric mixture will contain about 22% of the 1R-cis isomer and 78% of the 1S-trans isomer. The 1S-trans DV acid chloride that is used may be present in a mixture having an isomeric content of between about 0:100 to 21:79 of 1R-cis:1S-trans isomers. After the heating, the resulting mixture may be converted directly to a pyrethroid by esterification with 3-phenoxybenzyl alcohol, with the cyanohydrin of 3-phenoxybenzaldehyde or with any other alcohol which gives an insecticidal ester with the DV acid. The resulting pyrethroid composition enriched with the 1R-cis DV moiety will have greater insecticidal activity than the corresponding composition having more of the 1S-trans DV moiety. Alternatively, the unwanted 1S-trans intermediate can separated from its 1R-cis isomer. Specific methods of separating these diastereomers have been reported in U.S. Pat. Nos. 4,024,163 and 4,261,921. Also, other methods for separating diastereomers such as the DV acid derivatives and pyrethroid isomers are known to one skilled in the art. If separated, the 1S-trans intermediate may be recycled in the present process for another partial epimerization.

Using the same conditions as those described above for the epimerization of the 1S-trans isomer, the 1S-cis isomer undergoes epimerization to provide an isomeric mixture containing about 77% 1R-trans and 23% 1S-cis. The 1S-cis isomer that is used may be present in a mixture having an isomeric content of between about 0:100 to 76:24 of 1R-trans: 1S-cis isomers. The mixture may be directly converted to a pyrethroid or the 1S-cis isomer may be separated and recycled as discussed above.

The present process also has application in the preparation of other pyrethroids. For example, the process of the present invention is applicable to the preparation of 1R-cis or 1R-trans enriched mixtures of cyclopropanecarboxylic acids and their derivatives represented by formula I where A or B is chlorine and the other is trifluoromethyl, which are useful in the preparation of pyrethroids such as bifenthrin shown below. The present invention is also applicable to the preparation of 1R-cis or 1R-trans enriched mixtures of cyclopropanecarboxylic acids and their derivatives represented by formula I where A or B are both bromine, which are useful in the preparation of pyrethroids such as deltamethrin discussed above.

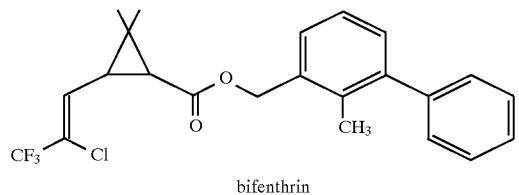

bifenthrin

The examples below show how the epimerization process of the present invention may be carried out to provide the 1R isomer.

EXAMPLE 1
1R-cis DV acid chloride

Thionyl chloride (1.15 g, 9 mmol) was added to 1S-trans 2,2-dimethyl-3-(2,2-chloroethenyl) cyclopropane-carboxylic acid (0.6 g, 3 mmol; $[\alpha]_{25° C.}$=–36.6, $CHCl_3$ ) under nitrogen and the mixture was stirred at room temperature for three hours. After removing excess thionyl chloride in vacuo, the 1S-trans DV acid chloride product was heated in a sealed ampoule at 145°–150° C. for four hours. Upon cooling, an aliquot of the reaction mixture was esterified with R-(-)-2-butanol [99%, $[\alpha]D$ –13°(neat)]. Capillary gas chromatography of the resulting diastereomeric ester mixture revealed that the isomerization had afforded a 22:78 mixture of 1R cis:1S-trans isomers of DV acid chloride.

EXAMPLE 2
1R-trans DV acid chloride

Thionyl chloride (0.85 g, 7 mmol) was added to 1S-cis 2,2-dimethyl-3-(2,2-chloroethenyl)cyclopropane-carboxylic acid (95% 1S-cis and 5% 1R-cis; 0.5 g, 2 mmol) under nitrogen and the mixture was stirred at room temperature for two hours. After removing excess thionyl chloride in vacuo, the cis DV acid chloride product was heated in a sealed ampoule at 145° C. for 3.5 hours. Upon cooling, an aliquot of the reaction mixture was esterified with R-(-)-2-butanol. Capillary gas chromatography of the resulting diastereomeric ester mixture revealed that the isomerization had afforded a 77:23 mixture of trans:cis isomers. The trans isomers were 94% 1R and 6% 1S and the cis isomers were 95% 1S and 5% 1R.

We claim:

1. A process for converting a first composition of a 2-(2,2-disubstitutedvinyl)-3,3-dimethylcyclopropane carboxylic acid derivative represented by the formula

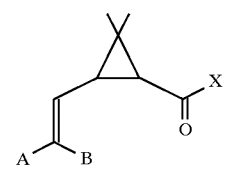

where both A and B are chlorine or bromine, or one of A and B is chlorine and the other is trifluoromethyl; and X is OH or $O_2C$-alkyl, to a second composition of the derivative, wherein the first composition has an isomeric content of between about 0:100 to 21:79 of 1R-cis:1S-trans isomers of the derivative and the second composition has an isomeric content of about 22:78 1R-cis:1S-trans isomers of the derivative which comprises the step of heating the first composition at a temperature between 140°–170° C. in the presence of a protic acid.

2. A process according to claim 1 wherein the derivative is heated in the presence of about 1% to 10% of a protic acid.

3. A process for converting a first composition of a 2-(2,2-disubstitutedvinyl)-3,3-dimethylcyclopropane carboxylic acid derivative represented by the formula

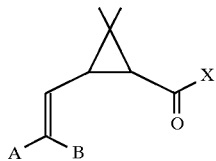

where both A and B are chlorine or bromine, or one of A and B is chlorine and the other is trifluoromethyl; and X is halogen, to a second composition of the derivative, wherein the first composition has an isomeric content of between about 0:100 to 21:79 of 1R-cis:1S-trans isomers of the derivative and the second composition has an isomeric content of about 22:78 1R-cis:1S-trans isomers of the derivative which comprises the step of heating the first composition at a temperature between 140°–170° C.

4. A process according to claim 3 wherein the heating is carried out without a solvent.

5. A process according to claim 4 wherein the heating is carried out at a temperature between 145°–150° C.

6. A process for converting a first composition of a 2-(2,2-disubstitutedvinyl)-3,3-dimethylcyclopropane carboxylic acid derivative represented by the formula

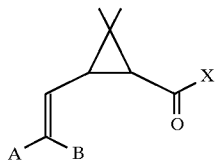

where both A and B are chlorine or bromine, or one of A and B is chlorine and the other is trifluoromethyl; and X is OH or O₂C-alkyl, to a second composition of the derivative, wherein the first composition has an isomeric content of between about 0:100 to 76:24 of 1R-trans:1S-cis isomers of the derivative and the second composition has an isomeric content of about 77:23 1R-trans:1S-cis isomers of the derivative which comprises the step of heating the first composition at a temperature range of 140°–170° C. in the presence of a protic acid.

7. A process according to claim 6 wherein the derivative is heated in the presence of about 1% to 10% of a protic acid.

8. A process for converting a first composition of a 2-(2,2-disubstitutedvinyl)-3,3-dimethylcyclopropane carboxylic acid derivative represented by the formula

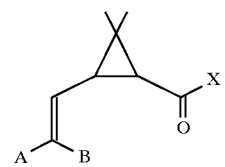

where both A and B are chlorine or bromine, or one of A and B is chlorine and the other is trifluoromethyl; and X is halogen, to a second composition of the derivative, wherein the first composition has an isomeric content of between about 0:100 to 76:24 of 1R-trans:1S-cis isomers of the derivative and the second composition has an isomeric content of about 77:23 1R-trans:1S-cis isomers of the derivative which comprises the step of heating the first composition at a temperature range of 140°–170°.

9. A process according to claim 8 wherein the heating is carried out without a solvent.

10. A process according to claim 9 wherein the heating is carried out at a temperature between 145°–150° C.

* * * * *